US008865466B2

(12) United States Patent
Borenstein et al.

(10) Patent No.: US 8,865,466 B2
(45) Date of Patent: Oct. 21, 2014

(54) NANOTOPOGRAPHIC COMPOSITIONS AND METHODS FOR CELLULAR ORGANIZATION IN TISSUE ENGINEERED STRUCTURES

(75) Inventors: Jeffrey T. Borenstein, Holliston, MA (US); David Carter, Cambridge, MA (US); Joseph P. Vacanti, Boston, MA (US)

(73) Assignees: The Charles Stark Draper Laboratory, Cambridge, MA (US); The General Hospital Corporation, Boston, MA (US)

( * ) Notice: Subject to any disclaimer, the term of this patent is extended or adjusted under 35 U.S.C. 154(b) by 267 days.

(21) Appl. No.: 13/350,749

(22) Filed: Jan. 14, 2012

(65) Prior Publication Data

US 2012/0122222 A1   May 17, 2012

Related U.S. Application Data

(62) Division of application No. 10/568,574, filed as application No. PCT/US2004/026848 on Aug. 18, 2004, now Pat. No. 8,097,456.

(60) Provisional application No. 60/495,973, filed on Aug. 18, 2003.

(51) Int. Cl.
*C12N 5/00* (2006.01)
*A61L 27/38* (2006.01)
*A61L 27/50* (2006.01)
*C12N 5/071* (2010.01)

(52) U.S. Cl.
CPC ............ *A61L 27/3886* (2013.01); *A61L 27/50* (2013.01); *C12N 5/0075* (2013.01); *C12N 2535/10* (2013.01); *C12N 5/067* (2013.01)
USPC ............................ 435/395; 435/373; 422/502

(58) Field of Classification Search
CPC ............................ C12N 5/0075; C12N 5/067
See application file for complete search history.

(56) References Cited

U.S. PATENT DOCUMENTS

| 3,684,097 A | 8/1972 | Mathewson, Jr. et al. |
| 3,839,204 A | 10/1974 | Ingenito et al. |
| 3,892,533 A | 7/1975 | Freedman et al. |
| 3,927,981 A | 12/1975 | Viannay et al. |
| 3,977,976 A | 8/1976 | Spaan et al. |
| 4,008,047 A | 2/1977 | Petersen |
| 4,176,069 A | 11/1979 | Metz et al. |

(Continued)

FOREIGN PATENT DOCUMENTS

| EP | 0246675 A1 | 11/1987 |
| WO | 9945860 A1 | 9/1999 |

(Continued)

OTHER PUBLICATIONS

Borenstein, et al: "Microfabrication technology for vascularized tissue engineering", Biomedical Microdevices Kluwer Academic Publishers, USA, vol. 4, No. 3, Jul. 2002, pp. 167-175.

(Continued)

*Primary Examiner* — Allison Ford
(74) *Attorney, Agent, or Firm* — Edwards Wildman Palmer LLP; George N. Chaclas

(57) ABSTRACT

The present invention relates to tissue engineered compositions and methods comprising nanotopographic surface topography ("nanotopography") for use in modulating the organization and/or function of multiple cell types.

20 Claims, 10 Drawing Sheets

(56) References Cited

U.S. PATENT DOCUMENTS

| | | | |
|---|---|---|---|
| 4,666,668 | A | 5/1987 | Lidorenko et al. |
| 5,034,188 | A | 7/1991 | Nakanishi et al. |
| 5,110,548 | A | 5/1992 | Montevecchi et al. |
| 5,222,982 | A | 6/1993 | Ommaya |
| 5,225,161 | A | 7/1993 | Mathewson et al. |
| 5,263,924 | A | 11/1993 | Mathewson |
| 5,316,724 | A | 5/1994 | Mathewson et al. |
| 5,626,759 | A | 5/1997 | Krantz et al. |
| 5,665,596 | A | 9/1997 | Mussi |
| 5,674,743 | A | 10/1997 | Ulmer |
| 5,695,717 | A | 12/1997 | Polaschegg et al. |
| 5,776,748 | A | 7/1998 | Singhvi et al. |
| 6,143,293 | A | 11/2000 | Weiss et al. |
| 6,368,838 | B1 | 4/2002 | Singhvi et al. |
| 6,372,482 | B1 | 4/2002 | Mitrani et al. |
| 6,720,469 | B1 | 4/2004 | Curtis et al. |
| 7,955,504 | B1 | 6/2011 | Jovanovic et al. |
| 8,128,822 | B2 | 3/2012 | Browning et al. |
| 8,137,554 | B2 | 3/2012 | Jovanovic et al. |
| 2002/0119176 | A1 | 8/2002 | Greenberg et al. |
| 2003/0129736 | A1 | 7/2003 | Mitrani |
| 2004/0057869 | A1 | 3/2004 | Dingley |
| 2007/0125489 | A1 | 6/2007 | Paul et al. |
| 2007/0281353 | A1 | 12/2007 | Vacanti et al. |
| 2010/0326914 | A1 | 12/2010 | Drost et al. |
| 2010/0326916 | A1 | 12/2010 | Wrazel et al. |
| 2012/0074062 | A1 | 3/2012 | Jovanovic et al. |

FOREIGN PATENT DOCUMENTS

| | | | |
|---|---|---|---|
| WO | 0038758 | A1 | 7/2000 |
| WO | 0066036 | A2 | 11/2000 |
| WO | 02076529 | A1 | 10/2002 |
| WO | 03082145 | A2 | 10/2003 |
| WO | 2004020341 | A2 | 3/2004 |
| WO | 2005034624 | A2 | 4/2005 |

OTHER PUBLICATIONS

Borenstein, et al., "Living Three-Dimensional Microfabricated Constructs for the Replacement of Vital Organ Function" Transducers 03 (2003).

Yasuda et al., "Fabrication of a Microfluidic Device for Axonal Growth Control" Transducers 03 (2003).

Wilson et al., "Surface Organization and Nonopatterning of Collagen by Dip-Pen Nanolithography" PNAS 98(24): 13660-13664 (2001).

Wilkinson et al., "The Use of Materials Patterned on a Nano- and - Micro-Metric Scale in Cellular Engineering" Materials and Science Engineering 19: 263-269 (2002).

Whitesides "The 'Right' Size in Nanobiotechnology" Nature Biotechnology 21(10): 1161-1165 (2003).

Xia et al., "Complex Optical Surfaces Formed by Replica Molding Against Elastomeric Masters", Science 273: 347-349 (1996).

Clark, et al., "Topographical Control of Cell Behavior: II. Multiple Grooved Substrata", Development 108: 635-644 (1990).

Clark et al., "Alignment of Myoblasts on Ultrafine Gratings Inhibits Fusion in Vitro", Int. J. Biochem. Cell Biol. 34: 816-825 (2002).

Clark et al., "Cell Guidance by Ultrafine Topography in Vitro" J. of Cell Sci. 99: 73-77 (1991).

Fleming et al., "Effects if Synthetic Micro- and Nano-Structured Surfaces on Cell Behavior", Biomaterials 20: 573-588 (1999).

Desai, "Micro and Nanoscale Structures for Tissue Engineering Constructs", Med. Eng. and Physics 22: 595-606 (2000).

Goodman "Three-Dimensional Extracellular Matrix Textured Biomaterials", Biomaterials 17 (21): 2087-2095 (1996).

Xia, et al., "Unconventional Methods for Fabricating and Patterning Nanostructures" Chem. Rev. 99: 1823-1848 (1999).

A

B

6/10

NANOTOPOGRAPHIC COMPOSITIONS AND METHODS FOR CELLULAR ORGANIZATION IN TISSUE ENGINEERED STRUCTURES

RELATED APPLICATIONS/PATENTS & INCORPORATION BY REFERENCE

This application is a division of U.S. application Ser. No. 10/568,574, filed Feb. 1, 2007, now U.S. Pat. No. 8,097,456, issued Jan. 17, 2012, which is the U.S. national phase, pursuant to 35 U.S.C. §371, of PCT international application Ser. No. PCT/US2004/026848, filed Aug. 18, 2004, designating the United States and published in English on Jul. 7, 2005 as publication WO 2005/060396 A2, which claims priority to U.S. provisional application Ser. No. 60/495,973, filed Aug. 18, 2003. The entire disclosures of the aforementioned patent applications are incorporated herein by this reference.

STATEMENT OF RIGHTS TO INVENTIONS MADE UNDER FEDERALLY SPONSORED RESEARCH

This work was funded by the United States Department of Defense Grant No. DAMD 17-99-2-9001. The government has certain rights to this invention.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference, and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

FIELD OF THE INVENTION

The present invention relates to tissue engineered compositions and methods having nanotopographic surface topography ("nanotopography") for use in modulating the organization and/or function of multiple cell types. Compositions of the invention are constructed using micromachining techniques to form microtopographic surfaces (e.g., surfaces comprising a plurality of channels). Nanotopographic patterns are then superimposed upon the channels to achieve the desired result.

BACKGROUND OF THE INVENTION

Tissue engineers have taken several approaches to generate replacement tissues and organs in the laboratory. Generally, autologous tissues are seeded onto a scaffold and expanded in culture. This scaffold should be biocompatible in order to avoid inflammatory responses and rejection of the implanted device, and may be biodegradable so that the artificial material is absorbed, leaving only natural tissue.

Scaffold fabrication techniques include an array of polymer processing techniques such as molding, casting, fiber mesh fabrication, and solid freeform fabrication. All of these methods lack the resolution necessary to fashion the finest features of the organ, such as the capillaries that predominate the circulatory supply. Microfabrication technology such as MEMS, including silicon micromachining and polymer replica molding, provides higher resolution for building tissue and organ scaffolds. The resolution of these techniques is in the 10 nm-1 micron range, which is typically in the range of what is necessary to configure the highest fidelity features of an organ.

The microfabrication process is inherently two-dimensional in nature, and therefore a three-dimensional tissue engineered device can be constructed by stacking multiple layers of cell sheets, optionally with microfabricated membranes interspersed between these layers (or within the individual channels). The interspersed membranes contain pores, which govern small molecule transport. The pore size, porosity and permeability of the membrane can be controlled to provide the desired effect for a particular structure or device.

Within the field of tissue engineering, present methods of achieving complex organization of multiple cell types include two broad general categories. One such class of methods entails the use of biochemical factors, chemical gradients, growth factors and other chemical means to arrange a variety of cells on a substrate (FIG. 1). These chemical techniques typically involve the micropatterning of a substrate for cell and tissue engineering with surface chemistries that enhance adhesion, growth, alignment and other behaviors of specific cell types, and to combine these micropatterns to build up clusters of varied cell types to form the microarchitecture of the target organ. One example of this approach is the use of appropriate growth and signaling factors to arrange endothelial cells and hepatocytes, among other cells, into the sinusoids that comprise the liver. Such methods include the use of self-assembled monolayers (alkenethiols), hydrophilic and hydrophobic patterns on surfaces, patterns of electric charges, thermally responsive polymers, polysaccharides, and cell adhesion factors such as laminin, extracellular matrix (ECM), aminosilanes, combinations of adhesive polymers, and cell growth factors.

The second broad class of methods utilizes precision loading of specific cell types into separate microengineered compartments within a tissue-engineered structure (FIG. 2). Such an approach typically utilizes microfluidic loading, either dynamically or statically, of a network of channels or vessels connected to form a cell compartment, and isolated by appropriate means from all other compartments. In sequential fashion, each compartment is loaded with the specific cell type, and communication between compartments controlled by porous or non-porous barriers (e.g., membranes). Properties of the barrier material are governed by the requirements of the specific cells and tissues in adjacent compartments. For instance, in the case of organ-specific cells such as hepatocytes contained in a compartment adjacent to the endothelial cells comprising the vascular supply, the barrier material, or membrane, physically separates the cell types from adjacent compartments during cell seeding, and readily enables the transfer of oxygen, nutrients and waste products between the two compartments.

The principal disadvantage of both of the aforementioned classes of existing techniques for producing complex tissue engineered structures is the challenge presented by the large, three-dimensional nature of the target tissue or organ for replication. These techniques work well and are quite efficacious when applied to laboratory-scale experimentation in which the resulting tissue-engineered product represents a relatively small assembly of perhaps hundreds or thousands of cells arranged within a single layer or a small number of stacked layers. However, replacement tissues and organs represent on the order of billions of cells of several different types, arranged in perhaps hundreds or thousands of layers.

The first class of methods, in which biochemical patterns are generated on engineered substrates, suffers from several drawbacks. First, there is a need to pattern each layer separately, a process not amenable to batch processing techniques such as lithography and molding, but rather to direct write deposition methods, which are difficult to scale up and accelerate. Therefore the chemical patterning process becomes a layer-by-layer challenge, in which a complex array of chemical factors must be sequentially deposited on each layer while precisely aligning to, and without disturbing, prior layers. Next, the method should be robust to three-dimensional assembly processes such as layer bonding and stacking, so that the three-dimensional assembly of the chemically patterned substrates does not disturb or harm the chemistries and patterns themselves. Finally, surface chemistries may interact with one another, through surface diffusion and other phenomena, thereby reducing or negating the efficacy of the approach.

The second class of methods, in which microfluidic culture of individual cell types is undertaken into a series of separate compartments, does not suffer from all of the same drawbacks as the chemical patterning technique. Since the compartment architecture controls the geometry and relative placement of the cell assemblies, the lack of robustness of chemical techniques is not an issue. Further, the three-dimensional assembly methods do not run the risk of harming the micropatterns, since they are robust physical geometries rather than chemical patterns. However, this microfluidic technique quickly becomes very complex when the number of cell types is increased, and places rigorous demands upon the network geometries. This is because the microfluidic compartments must be arranged in three-dimensions without crossing one another, and complex cell subassemblies may not be amenable to replication by interdigitated non-crossing channel networks. Therefore, techniques in which assemblies of cells can be created without regard to the complex nature of the compartment geometries is desired.

SUMMARY OF THE INVENTION

The present invention relates to tissue engineered compositions and methods comprising nanotopographic surface topography ("nanotopography") for use in modulating the organization and/or function of multiple cell types.

In one aspect, the invention is directed to a substrate having micromachined surface structures provided thereon, wherein said micromachined surface structures comprise nanotopographic features superimposed thereon, the nanotopographic features being arranged in such a manner so as to organize multiple cell types into desired subassemblies within said micromachined surface structures. This design provides at least two levels of control over cellular organization, in that the micromachined surface structures organize multiple cell types into desired assemblies and the nanotopographic features further organize the cell types into sub-assemblies.

In one embodiment, one or more micromachined surface structures defines the walls and floor of a channel. Accordingly, in one embodiment, the invention is directed to a substrate having micromachined surface structures provided thereon, wherein said micromachined surface structures comprise a plurality of channels having nanotopographic features superimposed thereon, the nanotopographic features being arranged in such a manner so as to organize multiple cell types into desired subassemblies within said channels.

Nanotopographic features of the invention can facilitate adhesion of one or more cell types. Accordingly, in one embodiment, the nanotopographic features are oriented to preferentially adhere one or more cell types to a desired location on the substrate.

Nanotopographic features of the invention can comprise various orientations, for example, to laterally align one or more cell types. In one embodiment, the nanotopographic features are oriented to form a grid.

Preferably, the nanotopographic features are generated by a lithographic technique, such as CCL.

In yet another aspect, the invention is directed to a method of organizing cells on a substrate for use in engineering tissue, said method comprising the steps of:
  a) generating micromachined surface structures; and
  b) superimposing nanotopographic features on the micromachined surface structures in such a manner so as to organize multiple cell types into desired subassemblies for use in constructing engineered tissue.

In one embodiment, the step of superimposing nanotopographic features includes arranging the nanotopographic features in predefined locations on the substrate. In yet another embodiment, superimposing nanotopographic features can include orienting the nanotopographic features to preferentially adhere one or more cell types to a desired location on the substrate.

In yet another aspect, the invention is directed to a tissue engineered system comprising one or more layers, wherein each layer includes micromachined surface structures having nanotopographic features superimposed thereon, the nanotopographic features being arranged in such a manner so as to organize multiple cell types into desired subassemblies within said micromachined surface structure.

In one embodiment, a semi-permeable membrane is positioned between the layers. In yet another embodiment, the channels are divided longitudinally into two compartments by a centrally positioned semi-permeable membrane, and wherein each compartment comprises a different cell type.

Tissue engineered systems of the invention can comprise a pumping means for circulating fluid through the system, and/or further comprise nutrient supply and excretion removal lines in fluid communication with the system.

Cell types of the invention include, but are not limited to endothelial cells, smooth or skeletal muscle cells, myocytes, cardiac cells, fibroblasts, chondrocytes, adipocytes, fibromyoblasts, ductile cells, skin cells, liver cells (e.g., hepatocytes), kidney cells, pancreatic cells (e.g., pancreatic islet cells), intestinal cells, osteoblasts, hematopoietic cells and stem cells.

BRIEF DESCRIPTION OF THE FIGURES

FIG. 5A depicts 105 nm lines on 300 nm pitch. FIG. 5B depicts 80 nm lines on 300 nm pitch.

FIG. 8 depicts bovine aortic endothelial cells cultured on nanotopographically patterned PDMS with a fibronectin coating.

DETAILED DESCRIPTION OF THE INVENTION

Figure 1:
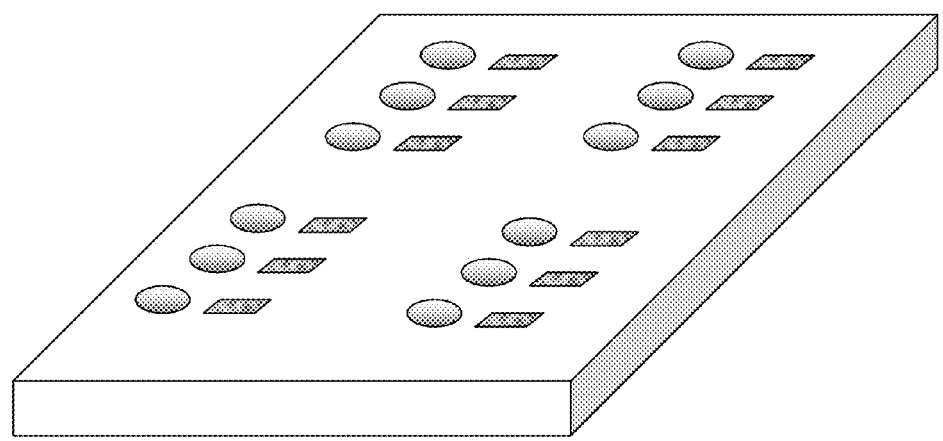
FIG. 1 illustrates a previous method for organizing cells into units with microarchitecture of an organ. The rectangular block represents a substrate for the cell co-culture. Oval regions represent one particular surface chemistry, such as a specific cell adhesion promoter, a cell of type "A," while the parallelograms represent a different cell adhesion promoter, a cell of type "B." This type of micropatterning results in a repeating unit of three adjacent cell type A-cell type B subunits across a surface, when exposed to a co-culture medium.
Figure 2:
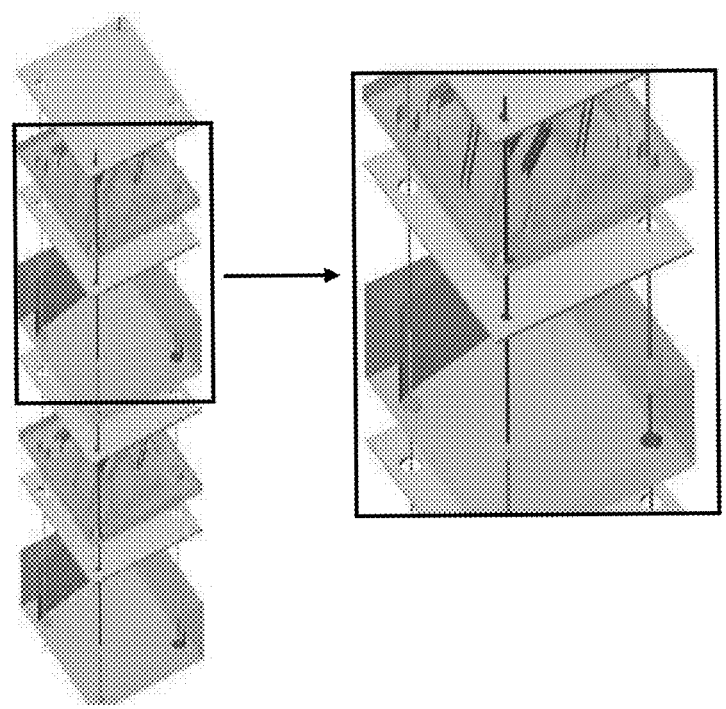
FIG. 2 depicts a schematic of yet another previous method for generating engineered tissue using co-culture. Rose-colored layer consists of vascular endothelial cell channels, which are separated from semi-transparent block containing organ-specific cells by the gray semipermeable membrane. Cell placement is achieved by separating channel networks for each cell type and filling them sequentially and separately.
Figure 3:
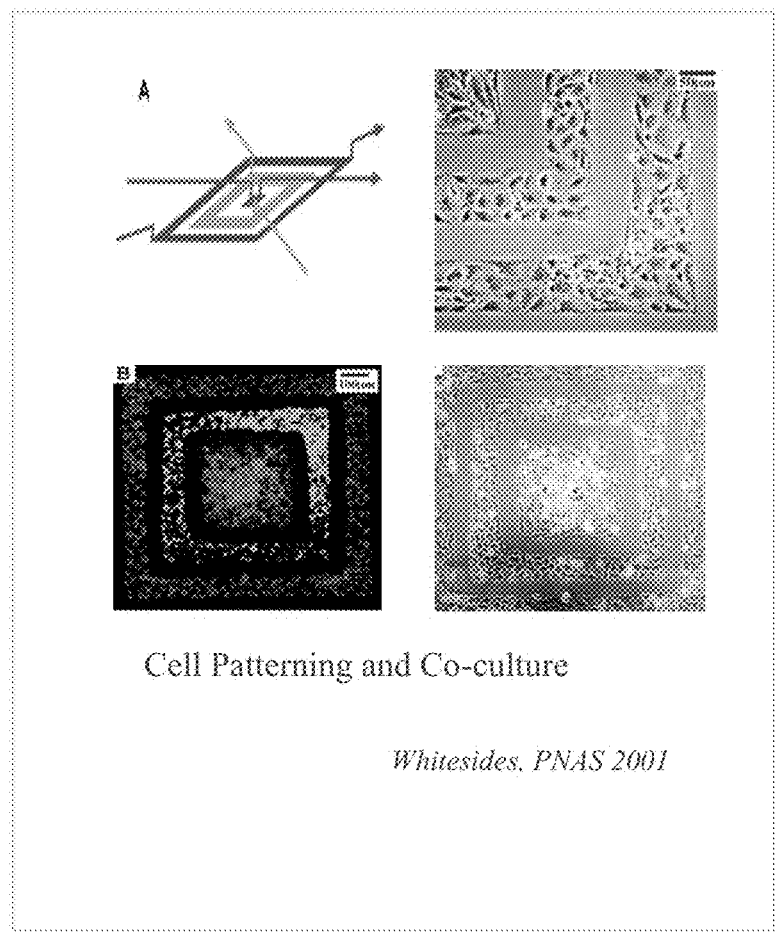
FIG. 3 depicts an image in which co-culture through patterning surface chemistry was achieved by Whitesides et al., Proc Natl Acad Sci USA. 97, (2002) the contents of which are incorporated here in by reference.
Figure 4:
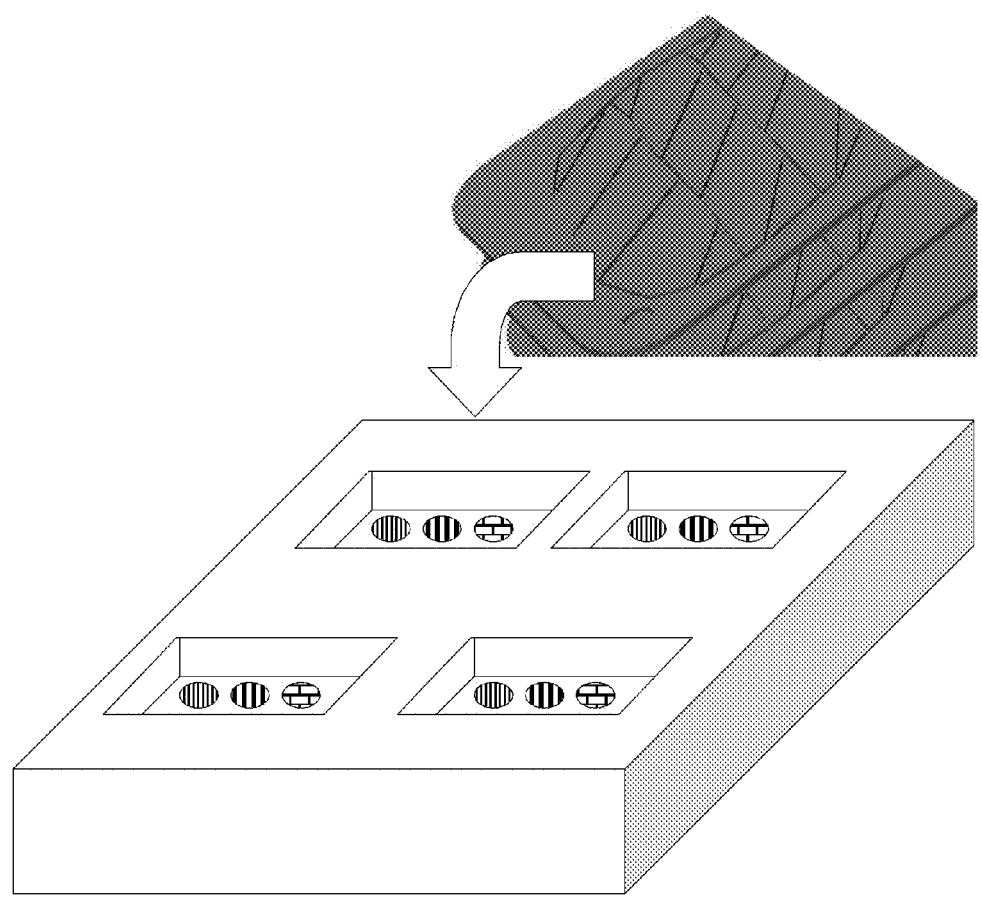
FIG. 4 depicts a schematic of how nanotopography can be superimposed upon tissue engineered structures of the invention. The rectangular block depicts machined compartments for organ-specific cells. Each nanotopographic feature provides a different level of adhesion for each cell type, and can therefore be used to generate cellular subunits for the microarchitecture of an organ. Aligned lithography and etching of the master mold either prior to or following the main compartment patterning and etching achieves the nanotopographic features. Optionally, an additional molding and bonding step with a completely separate channel network, generates the vascular compartment.

The present invention comprises compositions and methods wherein cells of differing types are compartmentalized upon surfaces comprising micropatterned topography.

I. Tissue Engineered Structures of the Invention

Nanotopographic patterning methods of the present invention can be applied to any microfabricated tissue engineered structure known in the art.

In a specific embodiment, nanotopographic patterning methods of the invention can be applied to the microfabricated tissue engineered structures described in U.S. Pat. No. 6,455,311, the contents of which are incorporated herein by reference.

In a yet another specific embodiment, nanotopographic patterning methods of the invention can be applied to the microfabricated tissue engineered structures described in U.S. patent application Ser. No. 10/187,247, the contents of which are incorporated herein by reference.

In a yet another specific embodiment, nanotopographic patterning methods of the invention can be applied to the microfabricated tissue engineered structures described in PCT Application No. US03/29880, filed Sep. 23, 2003, the contents of which are incorporated herein by reference.

In a yet another specific embodiment, nanotopographic patterning methods of the invention can be applied to the microfabricated tissue engineered structures described in PCT Application No. US04/16059, filed May 21, 2004, the contents of which are incorporated herein by reference.

A. Manufacture of Molds and Polymer Scaffolds

Tissue engineered structures of the invention can be comprised of one or more layers. Each layer of the system will have a support element that can comprise a mold. For purposes of this invention a "mold" is a device on the surface of which the branching structure of the microchannels is etched or formed. Fabrication of a mold begins by selection of an appropriate substrate. The choice of a substrate material is guided by many considerations, including the requirements placed on the fabrication process by the desired mold dimensions, the desired size of the ultimate template, and the surface properties of the wafer and their interaction with the various cell types, extracellular matrix ("ECM") and polymeric backbone. Also important are the thermal properties, such as the glass transition temperature (Tg), which must be high enough so that the network of pores in the mold does not collapse upon solvent removal if a thermal process is used to process the layers.

Molds of the present invention can comprise a variety of materials, including, but not limited to, inert materials such as silicon, polymers such as polyethylene vinyl acetate, polycarbonate, and polypropylene, and materials such as a ceramic or material such as hydroxyapatite. In particular, the mold can comprise from metals, ceramics, semiconductors, organics, polymers, and composites. Representative metals and semiconductors include pharmaceutical grade stainless steel, gold, titanium, nickel, iron, gold, tin, chromium, copper, alloys of these or other metals, silicon, silicon dioxide. These materials are either inherently suitable for the attachment and culture of animal cells or can be made suitable by coating with materials described herein to enhance cell attachment and culture (e.g. gelatin, matrigel, vitrogen and other tissue culture coatings known in the art).

MEMS replica molding can be used to make a "polymer scaffold" for seeding cells. In this method, a mold is made as described herein, preferably of silicon, and is then used as a template on which a polymeric material is cast. Optionally, the polymer scaffold can then be peeled away from the mold and seeded with cells.

A "tissue-defining surface" is the surface of a mold or a polymer scaffold.

The term "polymer" includes polymers and monomers that can be polymerized or adhered to form an integral unit. The polymer can be non-biodegradable or biodegradable, typically via hydrolysis or enzymatic cleavage. Biodegradable matrices are not typically preferred to construct molds, since they are not implanted and are preferably reusable. For implantation, polymer scaffolds are preferably used, more preferably biodegradable polymer scaffolds.

Preferably, the biodegradable polymer scaffold comprises biodegradable elastomers formed from hydrolyzable monomers as described in Wang et al, Nature Biotech 20, 602 (2002), the contents of which are incorporated herein by reference. These biodegradable elastomers are analogous to vulcanized rubber in that crosslinks in a three-dimensional network of random coils are formed. These biodegradable elastomers are hydrolyzed over time, preferably within 60 days.

Polymer material for implantation should be selected for biocompatibility. Any degradation products should also be biologically compatible. Relatively high rigidity is advantageous so that the polymer scaffold can withstand the contractile forces exerted by cells growing within the mold. A biologically compatible degradable polymer and its degradation products are non-toxic toward the recipient.

The term "biodegradable" refers to materials that are bioresorbable and/or degrade and/or break down by mechanical degradation upon interaction with a physiological environment into components that are metabolizable or excretable, over a period of time from minutes to three years, preferably less than one year, while maintaining the requisite structural integrity. As used in reference to polymers, the term "degrade" refers to cleavage of the polymer chain, such that the molecular weight stays approximately constant at the oligomer level and particles of polymer remain following degradation. The term "completely degrade" refers to cleavage of the polymer at the molecular level such that there is essentially complete loss of mass. The term "degrade" as used herein includes "completely degrade" unless otherwise indicated.

Materials suitable for polymer scaffold fabrication include, but are not limited to, poly-dimethyl-siloxane (PDMS), polyglycerol-sebacate (PGS), polylactic acid (PLA), poly-L-lactic acid (PLLA), poly-D-lactic acid (PDLA), polyglycolide, polyglycolic acid (PGA), polylactide-co-glycolide (PLGA), polydioxanone, polygluconate, polylactic acid-polyethylene oxide copolymers, modified cellulose, collagen, polyhydroxybutyrate, polyhydroxpriopionic acid, polyphosphoester, poly(alpha-hydroxy acid), polycaprolactone, polycarbonates, polyamides, polyanhydrides, polyamino acids, polyorthoesters, polyacetals, polycyanoacrylates, degradable urethanes, aliphatic polyesterspolyacrylates, polymethacrylate, acyl substituted cellulose acetates, non-degradable polyurethanes, polystyrenes, polyvinyl chloride, polyvinyl flouride, polyvinyl imidazole, chlorosulphonated polyolifins, polyethylene oxide, polyvinyl alcohol, Teflon®, nylon silicon, and shape memory materials, such as poly(styrene-block-butadiene), polynorbornene, hydrogels, metallic alloys, and oligo($\epsilon$-caprolactone)diol as switching segment/oligo(p-dioxyanone)diol as physical crosslink. Other suitable polymers can be obtained by reference to The Polymer Handbook, 3rd edition (Wiley, N.Y., 1989). Combinations of these polymers may also be used.

Polylactide-co-glycolides (PLGA), as well as polylactides (PLA) and polyglycolides (PGA) have been used to make biodegradable implants for drug delivery. See U.S. Pat. Nos. 6,183,781 and 6,733, 767 and references cited therein, the contents of which are specifically incorporated herein by reference. The ratio of lactide to glycolide of the poly(lactide-co-glycolide) copolymer can be, for example, 75:25, 60:40, 85:15 or 65:35. Biodegradable materials have been developed for use as implantable prostheses, as pastes, and as templates around which the body can regenerate various types of tissue. Polymers that are both biologically compatible and resorbable in vivo are known in the art as alternatives to autogenic or allogenic substitutes. In one embodiment, polymers are selected based on the ability of the polymer to elicit the appropriate biological response from cells, for example, attachment, migration, proliferation and gene expression.

Solvents for most of the thermoplastic polymers are known, for example, methylene chloride or other organic solvents. Organic and aqueous solvents for protein and polysaccharide polymers are also known. The binder can be the same material as is used in conventional powder processing methods or can be designed to ultimately yield the same binder through chemical or physical changes that occur as a result of heating, photopolymerization, or catalysis.

Properties of the mold and/or polymer scaffold surface can be manipulated through the inclusion of materials on the mold or in polymer scaffold material which alter cell attachment (for example, by altering the surface charge or structure), porosity, flexibility or rigidity (which may be desirable to facilitate removal of tissue constructs). Moreover, advances in polymer chemistry can aid in the mechanical tasks of lifting and folding as well as the biologic tasks of adhesion and gene expression. A "release layer" can be deposited onto the molds. The release layer can comprise materials such as, but not limited to, teflon-like layers generated by $C_4F_8$ plasma treatment. The release layer can be deposited in solid, liquid or vapor phase. Its main function is to reduce adhesion of the polymer replica to the master mold.

For example, molds can be coated with a unique temperature-responsive polymer, poly-N-isopropyl acrylamide (PNIPAAm), which demonstrates a fully expanded chain conformation below 32° C. and a collapsed, compact conformation at high temperatures. When grafted onto surfaces of silicon wafers using electron beam irradiation, it can be used as a temperature switch for creating hydrophilic surfaces below 32° C. and hydrophobic surfaces above 32° C. Since PNIPAAm is insoluble in water over the lower critical solution temperature (LCST about 32° C.) and reversibly solubilized below the LCST, cells detach from the substratum by simply lowering the temperature below the LCST. One of skill in the art can (1) engraft the polymer on silicon wafers that are pre-coated with polystyrene or (2) engraft the polymer on silicon wafers whose surface is first modified by vinyl-trichlolorosilane. Either of these techniques will ensure that the polymer is better integrated and conjugated to its substratum (polystyrene in the former case and vinyl groups in the later case) so that it can serve as an effective thermal switch, useful in reversing cell attachment and detachment as a single contiguous layer of cells without the usual cell damage.

Another system for promoting both cellular adhesion and lifting of cells as intact sheets can involve the use of RGD (Arg-Gly-Asp) peptides. The RGD sequence is part of the domain within the fibronectin molecule that endows it with the ability to interact with adhesion molecules present on the cell surface of fibroblasts. Fibronectin itself is a well-characterized extracellular, structural glycoprotein which interacts strongly with other extracellular matrix molecules and which causes the attachment and spreading of most cells. This function of the fibronectin molecule is localized primarily to the RGD sequence. One of skill in the art can synthesize RGD peptides with a structural backbone of PMMA that has an RGD peptide sequence at its tips, bound to one another with the intermediate layering of polyethylene oxide. This allows differential cell adhesion in only selected areas and not others. Once the tissue of desired quality is formed, release of this intact monolayer of tissue from its substratum is straightforward; it requires only the addition of soluble RGD to the culture medium to act as a competitive substrate to the insolubilized RGD substrate on the silicon mold surface.

In some embodiments, attachment of the cells to the mold and/or polymer scaffold is enhanced by coating the substrate with compounds such as basement membrane components, agar, agarose, gelatin, gum arabic, types I, II, III, IV, and V collagen, fibronectin, laminin, glycosaminoglycans, matrigel, vitrogen, mixtures thereof, and other materials known to those skilled in the art of cell culture.

Thus, by the methods of the invention, cells can be grown on molds that are uncoated or coated as described herein, depending upon the material used for mold construction.

Alternatively, cells can be grown on polymer scaffolds made by replica molding techniques.

B. Micromachining and Chemical Processing of Silicon and Other Mold Materials

Micromachining is a technique that produces grooves, slots, its, or more complex structures with precise dimensions in materials including semiconductors, such as silicon or gallium arsenide. This technology has been extensively utilized in diverse applications such as solar cells, high-value capacitors, solid-state inductors, and miniature gas chromatography systems. Micromachining begins with the production of a master pattern, which is reduced to the desired dimensions by a step-and-repeat photographic process to produce photomasks. The pattern on the photomask is transferred onto the silicon wafer by photolithography. The pattern on the silicon wafer is then etched to the desired depth by anisotropic etchants. The depth and spacing of an anisotropically etched surface can be regulated by the time of etching and the crystalline orientation of the silicon wafer.

As used herein, a "micromachined surface structure" refers to superficial structures created by a mechanical micromachining processes. Typically, micromachining is performed on standard bulk single crystal silicon wafers of a diameter ranging between about 50 and 300 millimeters (mm), preferably approximately 60 mm, and of thickness ranging between about 200 and 1200 μm. These wafers can be obtained from a large number of vendors of standard semiconductor material, and are sawn and polished to provide precise dimensions, uniform crystallographic orientation, and highly polished, optically flat surfaces. Wafers made from pyrex borosilicate or other glasses can also be procured and inserted into micromachining processes, with alternative processes used to etch the glassy materials.

Molds can be made by creating small mechanical structures in silicon, metal, polymer, and other materials using microfabrication processes. These microfabrication processes are based on well-established methods used to make integrated circuits and other microelectronic devices, augmented by additional methods developed by workers in the field of micromachining.

Microfabrication processes that can be used in making molds include lithography; etching techniques, such as lasers, plasma etching, photolithography, or chemical etching such as wet chemical, dry, and photoresist removal; or by solid free form techniques, including three-dimensional printing (3DP), stereolithography (SLA), selective laser sintering (SLS), ballistic particle manufacturing (BPM) and fusion deposition modeling (FDM); by micromachining; thermal oxidation of silicon; electroplating and electroless plating; diffusion processes, such as boron, phosphorus, arsenic, and antimony diffusion; ion implantation; film deposition, such as evaporation (filament, electron beam, flash, and shadowing and step coverage), sputtering, chemical vapor deposition (CVD), epitaxy (vapor phase, liquid phase, and molecular beam), electroplating, screen printing, lamination or by combinations thereof. See Jaeger, *Introduction to Microelectronic Fabrication* (Addison-Wesley Publishing Co., Reading Mass. 1988); Runyan, et al., Semiconductor Integrated Circuit Processing Technology (Addison-Wesley Publishing Co., Reading Mass. 1990); *Proceedings of the IEEE Micro Electro Mechanical Systems Conference* 1987-1998; Rai-Choudhury, ed., *Handbook of Microlithography, Micromachining & Microfabrication* (SPIE Optical Engineering Press, Bellingham, Wash. 1997), Borenstein et al, *Biomedical Microdevices* 4 (2002) p. 167. The selection of the material that is used as the mold determines how the surface is configured to form the branching structure. The following methods are preferred for making molds.

The geometry of the mold, in particular the number of different feature depths required, is the major factor determining the specific process sequence. The simplest case is that of a single depth dimension for the mold. Specifically, for a silicon substrate, one type of process sequence is as follows: first, the silicon wafer is cleaned, and a layer of photosensitive material is applied to the surface. Typically, the layer is spun on at a high revolution rate to obtain a coating of uniform thickness. The photoresist is baked, and the wafer is then exposed to ultraviolet or other short-wavelength light though a semi-transparent mask. This step can be accomplished using any one of several masking techniques, depending on the desired image resolution. The resist is then developed in appropriate developer chemistry, and the wafer is then hard-baked to remove excess solvent from the resist. Once the lithographic process has been completed, the wafer can be etched in a plasma reactor using one of several possible chemistries. Etching serves to transfer the two-dimensional pattern into the third dimension: a specified depth into the wafer. Plasma parameters are determined by the desired shape of the resulting trench (semi-circular, straight-walled profile, angled sidewall), as well as by the selectivity of the etchant for silicon over the masking photoresist. Once the etching has been completed, the photoresist can be removed and the wafer prepared for use in the tissue molding process.

Increased flexibility in the geometry of wafer mold can be obtained by inserting additional cycles of masking and etching. This modification provides the opportunity to machine channels of varying depths into the wafer mold. To design a mold that is suitable for the culturing of endothelial cells, increased flexibility is very important due to the need for vascular branches with different diameters. The techniques can be extended to provide as many additional layers and different depths as are desired. In addition, these techniques can be used to create secondary patterns within the pattern of microchannels. For example, it may be advantageous to have wells within the microchannels for culturing additional cell types such as feeder cells. The pattern of microchannels also can be designed to control cell growth, for example, to selectively control the differentiation of cells.

Another type of mold is fabricated simply through photolithography with no etching. The standard photoresist for this type of process, known as SU-8, is an epoxy resin negative resist material designed for use in conventional mask aligners. Resin viscosity can be adjusted to provide an enormous range of resultant thicknesses, providing layers as thin as 2 microns but as thick as 1 mm for various applications. Challenges involving film adhesion and cracking can be addressed by suitable process modifications.

One highly advantageous aspect of high aspect ratio photolithography is the ability to produce multiple pattern heights in the film, simply by using multiple exposures followed by a single development step, or other straightforward process variations. Feature geometry, such as the curvature of sidewalls at the top and bottom of structures, can be controlled by varying the baking parameters during processing. Subsequent adhesion of polymer films during replica de-molding is often low enough to enable ease of release, but plasma deposition equipment may be used to apply a thin mold release layer as required.

Glass and polymeric wafer molds can be fabricated using a similar sequence, but the actual process can be modified by the addition of an intervening masking layer, since etchants for these materials may attack photoresist as well. Such intervening materials simply function to transfer the pattern from the photoresist to interlayer and then on to the wafer below. For silicon etched in one of several wet chemistries, an intervening layer may also be necessary.

Molds formed of silicon dioxide can be made by oxidizing the surface of the silicon mold forms, rather than depositing a metal and then etching away the solid needle forms to leave the hollow silicon dioxide structures. In one embodiment, hollow, porous, or solid molds are provided with longitudinal grooves or other modifications to the exterior surface of the molds.

Polymeric molds can also be made using microfabrication. For example, the epoxy molds can be made as described above, and injection molding techniques can be applied to form the structures. These micromolding techniques are relatively less expensive to replicate than the other methods described herein.

Three dimensional printing (3DP) is described by Sachs, et al., *Manufacturing Review* 5, 117-126 (1992) and U.S. Pat. No. 5,204,055 to Sachs, et al. 3DP is used to create a solid object by ink-jet printing a binder into selected areas of sequentially deposited layers of powder. Each layer is created by spreading a thin layer of powder over the surface of a powder bed. The powder bed is supported by a piston, which descends upon powder spreading and printing of each layer (or, conversely, the ink jets and spreader are raised after printing of each layer and the bed remains stationary). Instructions for each layer are derived directly from a computer-aided design (CAD) representation of the component. The area to be printed is obtained by computing the area of intersection between the desired plane and the CAD representation of the object. The individual sliced segments or layers are joined to form the three-dimensional structure. The unbound powder supports temporarily unconnected portions of the component as the structure is built but is removed after completion of printing.

SFF methods other than 3DP that can be utilized to some degree as described herein are stereo-lithography (SLA), selective laser sintering (SLS), ballistic particle manufacturing (BPM), and fusion deposition modeling (FDM). SLA is based on the use of a focused ultra-violet (UV) laser that is vector scanned over the top of a bath of a photopolymerizable liquid polymer material. The UV laser causes the bath to polymerize where the laser beam strikes the surface of the bath, resulting in the creation of a first solid plastic layer at and just below the surface. The solid layer is then lowered into the bath and the laser generated polymerization process is repeated for the generation of the next layer, and so on, until a plurality of superimposed layers forming the desired apparatus is obtained. The most recently created layer in each case is always lowered to a position for the creation of the next layer slightly below the surface of the liquid bath. A system for stereolithography is made and sold by 3D Systems, Inc., of Valencia, Calif., which is readily adaptable for use with biologically compatible polymeric materials. SLS also uses a focused laser beam, but to sinter areas of a loosely compacted plastic powder, the powder being applied layer by layer. In this method, a thin layer of powder is spread evenly onto a flat surface with a roller mechanism. The powder is then raster-scanned with a high-power laser beam. The powder material that is struck by the laser beam is fused, while the other areas of powder remain dissociated. Successive layers of powder are deposited and raster-scanned, one on top of another, until an entire part is complete. Each layer is sintered deeply enough to bond it to the preceding layer. A suitable system adaptable for use in making medical devices is available from DTM Corporation of Austin, Tex.

BPM uses an ink-jet printing apparatus wherein an ink-jet stream of liquid polymer or polymer composite material is used to create three-dimensional objects under computer control, similar to the way an ink-jet printer produces two-dimensional graphic printing. The mold is formed by printing successive cross-sections, one layer after another, to a target using a cold welding or rapid solidification technique, which causes bonding between the particles and the successive layers. This approach as applied to metal or metal composites has been proposed by Automated Dynamic Corporation of Troy, N.Y. FDM employs an x-y plotter with a z motion to position an extrudable filament formed of a polymeric material, rendered fluid by heat or the presence of a solvent. A suitable system is available from Stratasys, Incorporated of Minneapolis, Minn.

The design of the channels in the mold can be constructed by a number of means, such as fractal mathematics, which can be converted by computers into two-dimensional arrays of branches and then etched onto wafers. Also, computers can model from live or preserved organ or tissue specimens three-dimensional vascular channels, convert to two-dimensional patterns and then help in the reconversion to a three-dimensional living vascularized structure. Techniques for producing the molds include techniques for fabrication of computer chips and microfabrication technologies. Other technologies include laser techniques.

C. Stacking Molds and/or Polymer Scaffolds to Achieve Three-Dimensionality

Fastening or sealing of the layers is required to be leak-proof and support fluid pressures necessary for dynamic cell seeding. Preferably, the layers are irreversibly bound before implantation into the host. Depending on the composition of the layered material, the layers can be sealed by solvent bonding; reflow by heating (40° C.); treating surface with oxygen plasma; or by polymer flow at the surface. Biologically compatible polymer materials maybe bonded together by plasma activation to form sealed structures (Jo et al., *SPIE* 3877, 222 (1999)). The basic process results in bonded layers with channel architecture closely resembling that obtained with silicon etched molds.

One common method used to seal micromachined wafers together is anodic bonding, a technique based on the high concentration of mobile ions in many glasses (Camporese, et al., *IEEE Electron. Device Lett. EDL* 2, 61 (1981)). This process produces a permanent seal; fracture testing of silicon-glass anodically bonded interfaces produces a failure within the bulk of the glass.

Etched wafers may be bonded together, producing closed lumens suitable for fluidic experiments. Alternatively, the multilayered device described by the present invention can be configured such that each of the layers has an alignment indentation on one surface of the layer and an alignment protrusion on the opposing surface of another layer. The alignment indentations can be shaped to mate with the alignment protrusion, so that the layers are held together.

To build up the mold and/or polymer scaffold layers by mechanical assembly, the layers can be mechanically mated using biodegradable or non-biodegradable barbs, pins, screws, clamps, staples, wires, string, or sutures. (See, U.S. Pat. No. 6,143,293.) With this mechanical assembly approach, each prefabricated section can comprise different mold and/or polymer scaffold material and/or different mold microstructures. Different sections of these can be seeded with cells before assembly. Cells thus be can be embedded into the mold or polymer scaffold by assembling sections around these components. In addition, surface features on each mold, which are readily fabricated, become part of the internal microstructure (e.g., molded surface channels become conduits for cell infusion, or for blood flow to stimulate angiogenesis). A surface feature on an individual mold or polymer scaffold will become an internal feature when another segment is assembled over it. For example, surface features such as channels can be micromachined into a first mold or polymer scaffold layer. When a second mold or polymer scaffold layer is placed atop that first layer, the micromachined surface feature becomes an internal feature of the apparatus. Connections between layers are achieved by integrating through-holes alongside the channel-like features in each layer. Through-holes connect in a specified way to the channel network, and connect with through-holes in the layers above and below.

D. Semi-Permeable Membrane

A semi-permeable membrane can be used to separate the cell types. In a layered device, a semi-permeable membrane can be used to separate the first mold or polymer scaffold from the second mold or polymer scaffold in the tissue engineered structures of the invention. Alternatively, each layer (as well as individual surfaced of a non-layered device) can comprise one or more channels having multiple cell types divided longitudinally by a centrally positioned membrane.

Preferably, the pore size of the membrane is smaller than the cell diameters, thus, cells will not be able to pass through (i.e. a low permeability for animal cells), while low molecular weight nutrients and fluids can pass through (i.e. a high permeability for nutrients), thereby providing adequate cell-to-cell signaling. Cell sizes vary but in general, they are in the range of microns. For example, a red blood cell has a diameter of 8 µm. Preferably, the average membrane pore size is on a submicron-scale to ensure effective screening of the cells.

The membrane can be made of a biologically compatible, nondegradable material such as cellulose, PolyDiMethylSiloxane (PDMS), PolyMethylMethacrylate (PMMA), PolyEtherSulfone (PES), PolySulfone (PS), PolyCarbonate (PC), or from a degradable material such as PLGA, PolyCaproLactone (PCL) or Biorubber, but the invention is not so limited.

Semi-permeable membranes of the present invention comprise a wide array of different membrane types and morphologies, which can be classified as follows:
(1) Track-etched membranes consisting of cylindrical through-holes in a dense polymer matrix. These membranes are typically made by ion-etching; or
(2) Fibrous membranes made by various deposition techniques of polymeric fibers. Production methods enable fibrous membranes to have specific molecular weight cut-offs.

Track-etch type membranes are preferred, as they limit the fluid motion in one direction. Preferably, fluid motion is in the vertical direction. Fibrous membranes permit fluid motion both laterally and vertically.

The development of an appropriate membrane will mirror the device progression. Biologically compatible and non-degradable membranes can be incorporated in microchannels that are made from poly(dimethyl siloxane) (PDMS). Since PDMS is non-degradable, the membranes do not need to be degradable either. However, degradable membranes and materials for microchannels can also be used. There exists a variety of commercial track-etched membranes with well-defined pore sizes that can be used for this purpose. Care must be taken to properly incorporate the membranes into the existing microchannels without leaking. To this end, the membranes can be bonded with either an oxygen plasma or a silicone-based adhesive. A small recession can be designed into the microchannels so that the membrane can fit tightly therein.

In principle, membrane formation from polymers relies on phase-phase separation. Polymer-solvent interactions are complex, and polymer phase diagrams are significantly more complicated than those for monomeric materials, e.g., metals. Phase separation can be induced either by diffusion (diffusion-induced phase separation or "DIPS") or by thermal means (thermal induced phase separation or "TIPS").

A DIPS system comprises polymer, solvent and non-solvent. The polymer solution is cast as a thin film and then immersed in a coagulation bath containing the non-solvent. This process is governed by the diffusion of various low molecular weight components. The exchange of solvent and non-solvent between the polymer solution and the coagulation bath leads to a change in the composition in the film and phase separation is induced. After some time, the composition of the polymer-rich phase reaches the glass transition composition and the system solidifies. To avoid macrovoid formation, a small amount of non-solvent can be mixed with the polymer solution. In a preferred embodiment, the polymer is polycaprolactone (PCL) and the separation system is chloroform/methanol. Specifically, a polymer solution with a concentration ranging from about 5-10% wt. is made. PCL is prepared by dissolving it in chloroform at room temperature under gentle stirring. Once the polymer has completely dissolved, a small amount is placed on a clean mirror surface, and a membrane knife is used to spread out a film with preset thickness. The thickness of the film can be adjusted by changing the gap between the knife blade and the mirror surface. Once the film has been spread, the entire mirror is immersed in a methanol bath. Phase separation occurs almost instantaneously, but the film and mirror are left in the coagulation bath for up to about 10 minutes to lock in the morphology. A typical membrane thickness is about 100 µm, and the pore size is on the order of about 1 µm, preferably between about 0.01 and 20 µm. Membrane morphology can be varied by altering the composition/concentration of the polymer solution, the film thickness, the components of the coagulation bath, and/or the process conditions. One skilled in the art would understand how to vary any one of these parameters to achieve the desired result.

A TIPS system comprises a thermal gradient to induce phase separation. By choosing a polymer-solvent system that is miscible at high temperatures, but immiscible at low temperatures, e.g., room temperature, phase separation can be induced upon cooling down the polymer solution. In a preferred embodiment, the polymer is PCL and the separation system is DMF/10% $C_3H_8O_3$.

II. Nanotopographic Patterns

Nanotopographic surface topography or "nanotopography" can enhance adhesion and cell alignment. Accordingly, nanotopographic patterns of the invention comprise periodic pattern arrays of grooves, grids, pores, and bumps of calculated dimensions. As used here in, the term "nanotopographic feature" refers to an individual unit of a nanopattern. A nanotopographic feature is a geometric structure having any shape (e.g., grooves, grids, pores, and bumps) which does not exceed 1 micron in height, width or diameter. In the lateral dimension, a nanotopographic feature can be less than 1 micron, e.g., about 25 nm-50 nm, 50 nm-100 nm, 100 nm-500 nm, 500 nm-900 nm. Height can span the same range and in specific embodiments, height steps between features are greater than 500 nm.

Periodicity of the nanotopographic features can be designed such that there are equal lines and spaces (e.g., 70 nm lines and spaces). It is also possible to have spaces much larger than the lines, if only a few lines (e.g., 70 nm lines), for instance, are needed to provide a desired effect, such as good adherence to a much larger cell. In this regard, designs can be provide increased space between the nanoscale grooves.

The choice of geometry and dimensions of nanotopographic patterns can be customized to achieve the desired tissue micro-architecture based on the empirical adherence of cells to a particular pattern. Nanotopographic patterning can be carried out according to methods known in the art, see, for example Goodberlet, Appl. Phy. Lett., 76 (2000) p. 667; Goodberlet, Appl. Phy. Lett., 81 (2002) p. 1315; Goodman et al, Biomaterials, 17 (1996) p. 2087; X. Sun et al, *J Vac Sci Tech* B 16(6) (1998) p. 3922; Wu et al, *J Vac Sci Technol* B 16(6) (1998) p. 3825; and Tan et al, *J Vac Sci Tech* B 16(6) (1998) p. 3926, the contents each of which are specifically incorporated herein by reference for the processes described.

According to methods of the invention, microtopographic surfaces are first patterned with microscale structures as described herein. As used here in, the term "microtopographic surface" refers to any surface mechanically patterned with microscale structures, such as channels. A nanotopographic pattern containing unit cells which preferentially generate adherence of specific cell types into organized subassemblies can then be aligned and superimposed on top of the channels. The layers are then stacked and bonded in the same manner as described herein, and multiple cell types are introduced into the constructs simultaneously.

Figure 5:
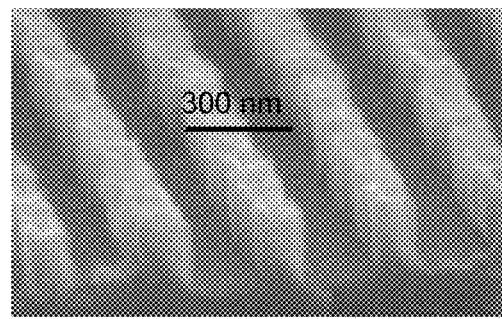
FIG. 5 depicts a nanopatterned XHRi-C polymer produced using conformable contact photolithography ("CCL"). Grating (line-space) features were patterned in XHRi-C antireflection coating polymer (Brewer Science, Rolla, Mo.) on a silicon wafer. These features were patterned in poly(methyl methacrylate (PMMA) photoresist by CCL replication from chrome-on-glass flex mask (XOPT, Geneva, Fla.). The pattern in the PMMA was transferred to a thin $SiO_2$ layer and then to the antireflection coating by RIE.
Figure 5:
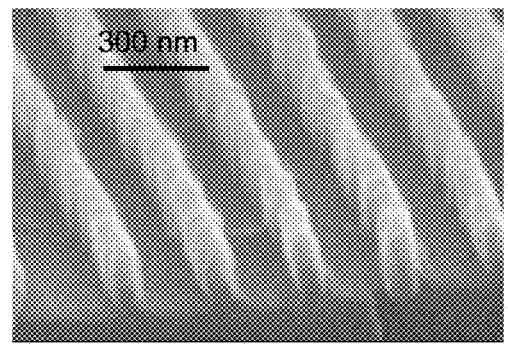
Figure 6:
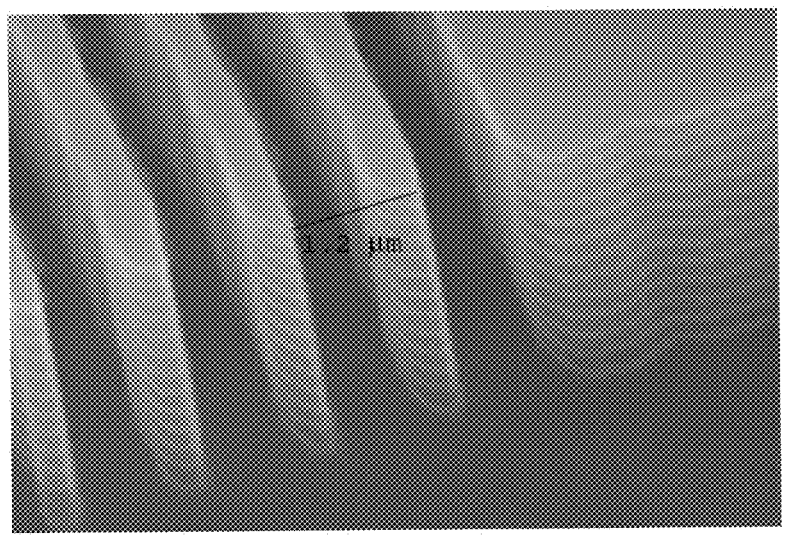
FIG. 6 depicts 400 nm wide by 4.2 μm high structure patterned by deep RIE ("DRIE") in silicon. Scalloped edges are due to the cyclic nature of the process (i.e., etch/protect/etch/protect) of the DRIE process.
Figure 7:
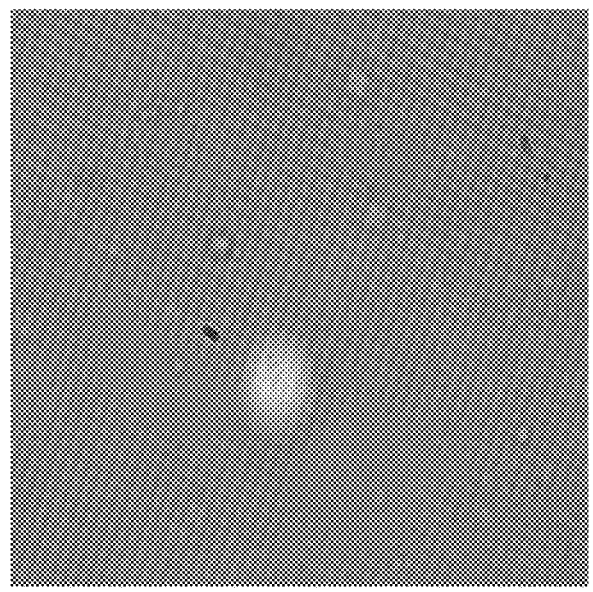
FIG. 7 depicts bovine aortic endothelial cells cultured on nanopatterned PDMS. High structures (700 nm wide×300 nm) on 3.5 μm pitch were molded into PDMS from an etched $SiO_2$ mold.
Figure 8A:
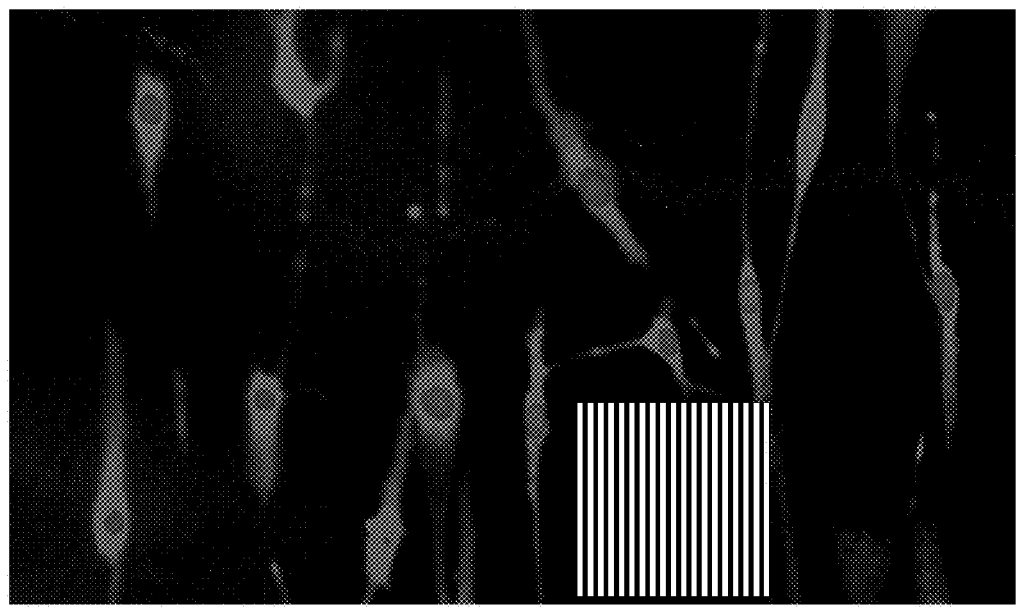
FIG. 8A depicts alignment on lateral grooves (900 nm).
Figure 8B:
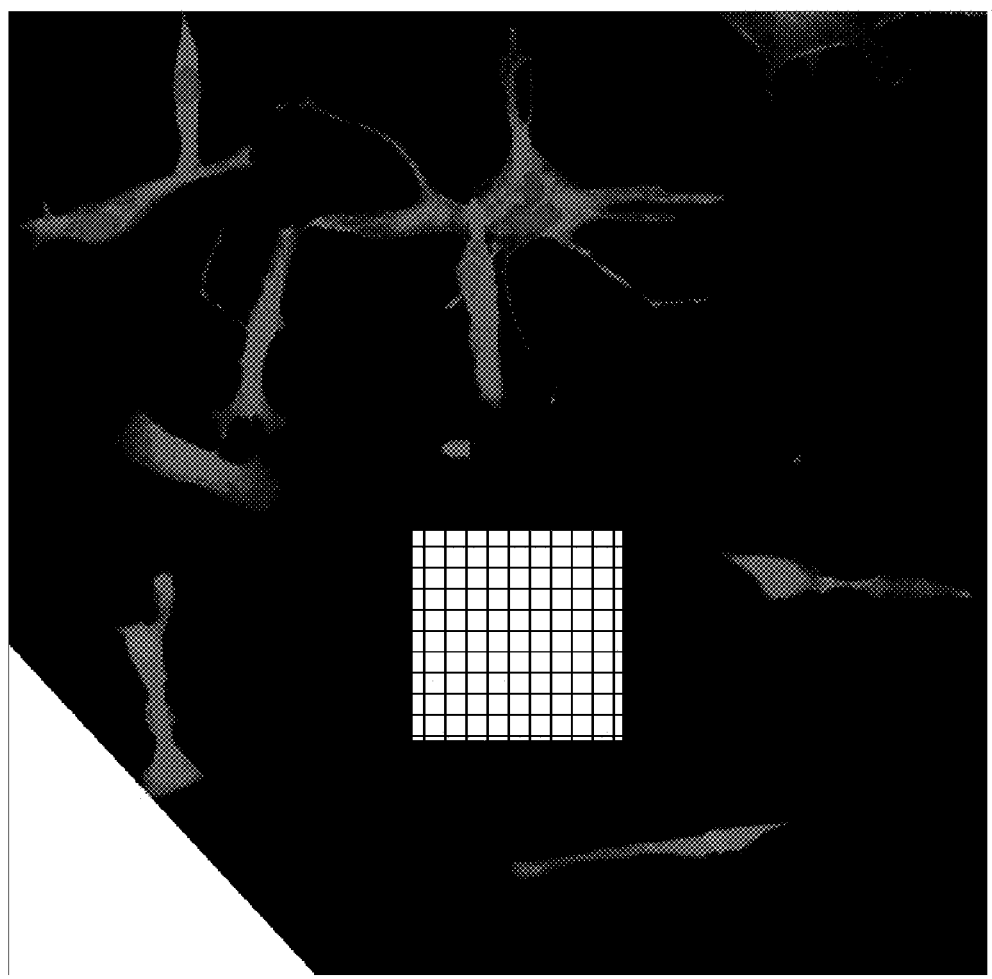
FIG. 8B depicts orientation on a grid (800 nm). By comparison.
Figure 8C:
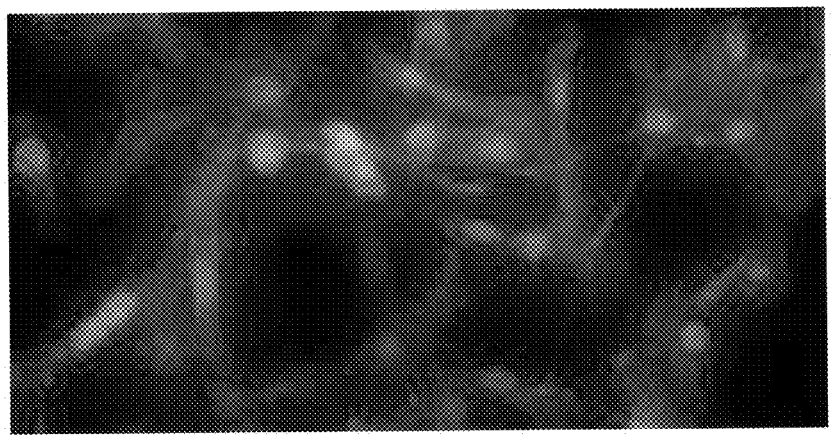
FIG. 8C depicts randomly orientated endothelium on an ungrooved surface (control).

Nanopatterning can be performed, for example, using conformable contact lithography ("CCL"), which can generate 50 nm feature sizes (Goodberlet, *Appl. Phy. Lett.,* 76 (2000) p. 667, Goodberlet, *Appl. Phy. Lett.,* 81 (2002) p. 1315). To form nanopatterned surfaces, top-down nanolithography can be combined with MEMS device fabrication techniques, such as reactive ion etching ("RIE"). In specific embodiments, gratings can be etched into a silicon substrate using silicon deep RIE ("DRIE") (Ayon et al, *J Vac Sci. Tech.* 18 (2000) p. 1412). The DRIE process is preferable for high-aspect-ratio MEMS structures. These techniques can be used to either directly form patterned substrates or patterned polymers on substrates, or to create molds which will be used to create replicas in polymers. FIG. 5 provides an example of direct patterning of a polymer. XHRi-C antireflection coating, for example, can be used as an etch mask for the underlying substrate. The etched substrate (silicon, $SiO_2$, or another material) can then be used as a surface for cell growth, or used to mold nanotopographic features into polymers.

Either non-deterministic patterning or deterministic techniques, can be used. Non-deterministic patterning techniques include, but are not limited to, gold colloid deposition (Curtis et al, *Biophys. Chem.* 94 (2001) p. 275, Dalby et al, *Experimental Cell Research* 276 (2002) p. 1, Riehle et al, *Mat. Res. Soc. Symp. Proc.* 705 (2002) Y.5.1.1, Dalby et al, *Tissue Engineering* 8 (2002) p. 1099, Dalby et al, *Biomaterials* 23 (2002) p. 2945 and Dalby et al, *Biomaterials* 24 (2003) p. 927) and randomly-patterned "silicon grass" (Turner et al, *J Vac Sci Technol.* 15 (1997) p. 2848).

Deterministic patterning techniques include, but are not limited to, electron-beam lithography (Rajinicek et al, *J. Cell Sci.* 100 (1997) p. 2905, Curtis et al, *Biophys. Chem.* 94 (2001) p. 275, Riehle et al, Mat. Res. Soc. Symp. Proc. 705 (2002) Y.5.1.1), and nanoimprint lithography (Chou et al, *Science* 272 (1996) p. 85, Xia et al, *Chem. Int. Ed.* 37 (1998) p. 550, Michel et al, *IBM J. Res. Dev.* 45 (2001) p. 697).

In a specific embodiment, CCL is a preferred technique for generating patterns having nanotopographic features. CCL enables the production of nanotopographic patterns as small as 50 nm or below. CCL can be used to create one and two dimensional lateral feature sizes ranging from 50-100 nm up to several microns, and with a feature periodicity as small as 200 nm. CCL can be used in combination with RIE to create surfaces with vertical dimensions from a few nanometers to a few hundred nanometers. These surfaces can be used for cell growth and be used as molds to pattern polymers.

Once seeded, the cells will organize into the desired microarchitecture through the contact guidance phenomenon, which, as applied to tissue engineered structures of the invention, involves on the ability of nanoscale surface topography to "switch on" or "switch off" cell adhesion of various cell types. For a further description of this phenomenon, see, for example U.S. Pat. Nos. 6,720,469, 6,368,838, and 5,776, 748; Flemming et al, *Biomaterials* 20 (1999) p. 573, Desai, *Med. Eng. Phys.* 22 (2000) p. 595, Goodman et al, *Biomaterials* 17 (1996) p. 2087. Xia et al, *Chem. Rev.* 99 (1996) p. 1823, Whitesides, *Nat. Biotechnol.* 21 (2003) p. 1161, Xia et al, *Development* 108 (1990) p. 635, Clark, P. et al, *Int. J. Biochem. Cell. Biol.* 34 (2002) p. 816 and Clark, P. et al *J. Cell Sci.* 99 (1991) p. 73.

The type, size, and periodicity of the pattern features can influence a specific cell function. It is known in the art that organizing cells in specific arrangements can lead to a desired physiological behavior (see, for example Bhatia et al, *J. Biomed. Mater. Res.* 34 (1997) p. 89; Bhatia et al, *Biotechnol. Prog.* 14 (1998) p. 378 and Bhatia et al, *FASEB J.,* 13 (1999) p. 1884, the contents of which are incorporated herein by reference). Such arrangements can be provided by the microtopographic and nanotopographic designs of the invention. Standard assays known in the art can be performed to quantify the ability of fabricated and patterned surfaces to modulate fundamental cell behaviors such as proliferation, adhesion, migration, and differentiation. Cells can be labeled and monitored for functional activity. For a description of probes for use in cell labeling see, for example Molecular Probes Handbook, Chapter 11, (2004) Invitrogen Detection Technologies. http://www.probes.com/handbook/sections/1100.html.

In yet a further embodiment, nanopatterning can selectively control the adhesion of precursors such as proteins, cell adhesion molecules, etc., so that these precursors could be positioned accurately and subsequently guide the placement of specific cell types to their appropriate locations.

In alternate embodiments of the invention, microtopographic and nanotopographic patterning techniques are combined with methods known in the art.

In one embodiment, multiple microfluidic compartments are combined with nanopatterning in order to organize multiple cell types. In this regard, the microchannels can be defined by creating a micromachined master mold, and then generating inverse replica molded polymer scaffolds with the microchannels in a desired geometric or network structure. To provide a nanotopographic surface for control of cells, the nanoscale features are superimposed on the surface of the master mold wafer in the areas that are not etched down. As a result, a mold wafer with nanotopography on the top (unetched) surface is present. The nanotopography need not be present where the silicon mold wafer is etched down to define the mold geometry for the microchannels. When the polymer is replica-molded from the master mold, the inverse geometry is created, and therefore, the top surface of the polymer (corresponding to the channels in the master) is not patterned, but the microchannel surface of the polymer has the image of the nanopatterned top surface of the master mold.

In yet another embodiment, surface chemical patterning is used in combination with nanotopographic patterning to provide further cell control. In this regard, surface patterns on the microchannels are utilized in addition to nanotopographic control to localize and organize different cell types. For example, distinct areas of the channels can be superimposed with nanotopography while other areas can have surface chemical species patterned thereon. Methods of surface chemical patterning are well known in the art, and can be generally applied by the skilled artisan to tissue engineered systems of the invention.

III. Cells

Many examples of co-culture-driven engineered tissues exist. Among them are co-cultures of hepatocytes and fibroblasts, along with endothelial cells, for growth of liver tissue. Another example involves co-culture of smooth muscle cells along with an organ-specific cell type. A third example involves Kupffer cells and biliary duct cells. Co-culture of endothelial and epithelial cells represents another potential target.

In one embodiment, methods of the invention can be used to preferentially align particular cell types (e.g. muscle or nerve) in addition to maintaining them in desired locations. In this regard, the dimensionality and/or orientation of the nanotopographic pattern on a surface is used to preferentially bind different cell types during a single or multiple microfluidic seeding cycles.

The pattern orientation with respect to the direction of flow comprises another means of organizing cellular units. Nanotopography can enhance adhesion and cell alignment. However, under some conditions, adhesion is not regulated by topography alone. In this instance, cell adhesion is viewed as a matter of gradation; cell positioning and organization is therefore achieved by governance of a threshold for adhesion. Microfluidic cell culture can benefit from this approach, as the goal of microfluidic cell culture is to cause cells to adhere to the walls of channels during controlled flow of cell-containing medium. Whereas the flow used to introduce cells to the network can cause previously adherent cells to detach, others will be maintained in position. In specific embodiments, this phenomenon can be used to provide a controlled threshold for the adhesion of a particular cell type, while other co-cultured cell types are selectively targeted for disassociation. It is well within the level of skill in the art to vary the parameters of the pattern to maintain all desired cell types, or preferentially select one cell type over another. For example, it can be desirable to maintain several cell types, having varying degrees of adherence. Once a particular cell type has attached to the "high adhesion" sites (as controlled by patterned nanotopography), the next set of cells can be located on the next set of targeted locations using a lower controlled flow rate.

A. Cell Seeding

Within a single layer of the system, microscale channels (which can be optionally divided into two compartments by a membrane), contain functional, mesenchymal or parenchymal cells, such as smooth or skeletal muscle cells, myocytes (muscle stem cells), fibroblasts, chondrocytes, adipocytes, fibromyoblasts, ectodermal cells, including ductile and skin cells, hepatocytes, kidney cells, pancreatic islet cells, cells present in the intestine, and other parenchymal cells, osteoblasts and other cells forming bone or cartilage, and hematopoietic cells. In some cases it may also be desirable to include nerve cells. "Parenchymal cells" include the functional elements of an organ (e.g., organ-specific cells), as distinguished from the framework or stroma. "Mesenchymal cells" include connective and supporting tissues, smooth muscle, vascular endothelium and blood cells.

The membrane dividing the cells (either between layers, or within individual channels, for example) allows gas exchange, diffusion of nutrients, and waste removal. Thus, one compartment or layer comprises the circulation through which blood, plasma or media with appropriate levels of oxygen can be continuously circulated to nourish the second compartment. The second compartment or layer comprises a reservoir for functional cells of one or more organs. The system optionally includes inlets for neural inervation, urine flow, biliary excretion or other activity.

Cells can be obtained by biopsy or harvest from a living donor, cell culture, or autopsy, all techniques well known in the art. Cells are preferably autologous. Cells to be implanted can be dissociated using standard techniques such as digestion with a collagenase, trypsin or other protease solution and are then seeded into the mold or polymer scaffold immediately or after being maintained in culture. Cells can be normal or genetically engineered to provide additional or normal function. Immunologically inert cells, such as embryonic or fetal cells, stem cells, and cells genetically engineered to avoid the need for immunosuppression can also be used. Methods and drugs for immunosuppression are known to those skilled in the art of transplantation.

Molecules such as growth factors or hormones can be covalently attached to the surface of the molds and/or polymer scaffolds and/or semi-permeable membrane to effect growth, division, differentiation or maturation of cells cultured thereon.

Preferably, hepatocytes can be used with this invention. The hepatocytes can be highly proliferative hepatocytes, known as small hepatocytes (SHCs), which have the ability to proliferate in vitro for long periods of time (Mitaka, et al., *Biochem Biophys Res Commun* 214, 310 (1995); Taneto, et al, *Am J Pathol* 148, 383 (1996)). Small hepatocytes express hepatocyte specific functions such as albumin production (Mitaka, et al., *Hepatology* 29, 111 (1999)).

Undifferentiated or partially differentiated precursor cells, such as embryonic germ cells (Gearhart, et al., U.S. Pat. No. 6,245,566), embryonic stem cells (Thomson, U.S. Pat. Nos. 5,843,780 and 6,200,802), mesenchymal stem cells (Caplan, et al. U.S. Pat. No. 5,486,359), neural stem cells (Anderson, et al., U.S. Pat. No. 5,849,553), hematopoietic stem cells (Tsukamoto, U.S. Pat. No. 5,061,620), multipotent adult stem cells (Furcht, et al., WO 01/11011) can be used in this invention. Cells can be kept in an undifferentiated state by co-culture with a fibroblast feeder layer (Thomson, U.S. Pat. Nos. 5,843,780 and 6,200,802), or by feeder-free culture with fibroblast conditioned media (Xu, et al. *Nat. Biotechnol.*, 19, 971 (2001)). Undifferentiated or partially differentiated precursor cells can be induced down a particular developmental pathway by culture in medium containing growth factors or other cell-type specific induction factors or agents known in the art. Some examples of such factors are shown in Table 1.

TABLE 1

Selected Examples of Differentiation Inducing Agents

| Agent | Progenitor | Differentiated Cell |
|---|---|---|
| Vascular Endothelial Growth Factor | Embryonic Stem Cell | Hematopoietic Cell[1] |
| Sonic Hedgehog | Floor Plate | Motor Neuron[2] |
| Insulin-like Growth Factor II | Embryonic Stem Cell | Myoblast[3] |
| Osteogenin | Osteoprogenitor | Osteoblast[4] |
| Cytotoxic T Cell Differentiation Factor | Spleen Cell | Cytotoxic T Lymphocyte[5] |
| β-catenin | Skin Stem Cell | Follicular Keratinocyte[6] |
| Bone Morphogenic Protein 2 | Mesenchymal Stem Cell | Adipocytes, Osteoblasts[7] |
| Interleukin 2 | Bone Marrow Precursor | Natural Killer Cells[8] |
| Transforming Growth | Cardiac Fibroblast | Cardiac Myocyte[9] |

TABLE 1-continued

Selected Examples of Differentiation Inducing Agents

| Agent | Progenitor | Differentiated Cell |
|---|---|---|
| Factor □ | | |
| Nerve Growth Factor | Chromaffin Cell | Sympathetic Neuron[10] |
| Steel Factor | Neural Crest | Melanocyte[11] |
| Interleukin 1 | Mesencephalic Progenitor | Dopaminergic Neuron[12] |
| Fibroblast Growth Factor 2 | GHFT | Lactotrope[13] |
| Retinoic Acid | Promyelocytic Leukemia | Granulocyte[14] |
| Wnt3 | Embryonic Stem Cell | Hematopoietic Cell[15] |

[1]Keller, et al. (1999) *Exp. Hematol* 27: 777-787.
[2]Marti, et al. (1995) *Nature*. 375: 322-325.
[3]Prelle, et al. (2000) *Biochem. Biophy. Res. Commun.* 277: 631-638.
[4]Amedee, et al. (1994) *Differentiation*. 58: 157-164.
[5]Hardt, et al. (1985) *Eur. J. Immunol*. 15: 472-478.
[6]Huelsken, et al. (2001) *Cell*. 105: 533-545.
[7]Ji, et al. (2000) *J. Bone Miner. Metab*. 18: 132-139.
[8]Migliorati, et al. (1987) *J. Immunol*. 138: 3618-3625.
[9]Eghbali, et al. (1991) *Proc. Natl. Acad. Sci. USA*. 88: 795-799.
[10]Niijima, et al. (1995) *J. Neurosci*. 15: 1180-1194.
[11]Guo, et al. (1997) *Dev. Biol*. 184: 61-69.
[12]Ling, et al. (1998) *Exp. Neurol*. 149: 411-423.
[13]Lopez-Fernandez, et al. (2000) *J. Biol. Chem*. 275: 21653-60.
[14]Wang, et al. (1989) *Leuk. Res*. 13: 1091-1097.
[15]Lako, et al. (2001) *Mech. Dev*. 103: 49-59.

A stem cell can be any known in the art, including, but not limited to, embryonic stem cells, adult stem cells, neural stem cells, muscle stem cells, hematopoietic stem cells, mesenchymal stem cells, peripheral blood stem cells and cardiac stem cells. Preferably, the stem cell is human. A "stem cell" is a pluripotent, multipotent or totipotent cell that can undergo self-renewing cell division to give rise to phenotypically and genotypically identical daughter cells for an indefinite time and can ultimately differentiate into at least one final cell type.

The quintessential stem cell is the embryonic stem cell (ES), as it has unlimited self-renewal and multipotent and/or pluripotent differentiation potential, thus possessing the capability of developing into any organ, tissue type or cell type. These cells can be derived from the inner cell mass of the blastocyst, or can be derived from the primordial germ cells from a post-implantation embryo (embryonal germ cells or EG cells). ES and EG cells have been derived from mice, and more recently also from non-human primates and humans. Evans et al. (1981) Nature 292:154-156; Matsui et al. (1991) Nature 353:750-2; Thomson et al. (1995) Proc. Natl. Acad. Sci. USA. 92:7844-8; Thomson et al. (1998) Science 282:1145-1147; and Shamblott et al. (1998) Proc. Natl. Acad. Sci. USA 95:13726-31.

The terms "stem cells," "embryonic stem cells," "adult stem cells," "progenitor cells" and "progenitor cell populations" are to be understood as meaning in accordance with the present invention cells that can be derived from any source of adult tissue or organ and can replicate as undifferentiated or lineage committed cells and have the potential to differentiate into at least one, preferably multiple, cell lineages.

B. Methods for Seeding Cells into Molds or Polymer Scaffolds

After a mold with the desired high degree of micromachining and nanopatterning is prepared, the molds themselves or polymer scaffolds are seeded with the desired cells or sets of cells. The distribution of cells throughout the mold or polymer scaffold can influence both (1) the development of a vascularized network, and (2) the successful integration of the vascular device with the host. The approach used in this invention is to provide a mechanism for the ordered distribution of cells onto the mold or polymer scaffold. Cells that are enriched for extracellular matrix molecules or for peptides that enhance cell adhesion can be used. Cells can be seeded onto the mold or polymer scaffold in an ordered manner using methods known in the art, for example, King et al, *Proceedings of the Micro TAS Conference*, Monterey, Calif., (2001); Teebken, et al., *Eur J. Vasa Endovasc. Surg*. 19, 381 (2000); Ranucci, et al., *Biomaterials* 21, 783 (2000). Also, tissue-engineered devices can be improved by seeding cells throughout the structure and allowing the cells to proliferate in vitro for a predetermined amount of time before implantation, using the methods of Burg et al., *J. Biomed. Mater. Res* 51, 642 (2000).

Seeding of each cell type is done by providing cells to each compartment separately using microfluidic techniques. For example, endothelial cells are introduced into the inlet of the vascular network, and prevented from crossing over to a parenchymal compartment by virtue of the small pores connecting the compartments. Other compartments are filled by the same means, keeping cell types in the desired locations.

In one embodiment, the mold is first seeded with parenchymal cells, such as hepatocytes or renal cells (e.g., proximal tubule cells). Cells can be maintained in culture for a week or so in order to obtain a population doubling. It can be maintained in a perfusion bioreactor to ensure adequate oxygen supply to the cells in the interior. The system is then seeded with endothelial cells and cultured further. In regions where the matrix is resorbed rapidly, the tissue can expand and become permeated with capillaries.

C. Cell Seeding of Horizontal Layer By Laminar Flow

Cell seeding can be performed by slow flow. As a practical matter, the geometry of the system will determine the flow rates. In general, endothelial cells can enter and form vessel walls in micromachined channels that are about 10-50 µm, and upon which nanotopographic patterns of the invention have been placed. Thus, in addition to serving as a mechanical framework for the organ, the assembled system provides a template for all of the microstructural complexity of the organ, so that cells have a mechanical map to locate themselves and form subsystems, such as blood vessels in the liver.

Micromachined channels in the horizontal direction typically proceed from larger to smaller to larger. The geometries can be as complex as desired in-plane (horizontal direction). Thus, one can use small geometries in-plane (such as horizontal conduits of about 5-20 µm). The alignment of through-holes creates vertical conduits or channels in the z-axis. However, the vertical channels need not go from larger to smaller to larger. In the vertical direction, the vertical channels can be parallel to each other and have diameters on the micron level, large enough only to allow cell seeding (e.g., hepatocytes are about 40 µm). In one embodiment, different types of cells are seeded horizontally onto different layers of the assembled apparatus. In another embodiment, the different types of cells are seeded using pores or channels from different directions. Various combinations are also possible.

IV. Methods of Use

The systems of the invention can be implanted into a subject to supplement or replace the biological function of a tissue or organ. Alternatively, the systems can remain ex vivo, serving as extracorporeal devices to supplement or replace biological function. As used herein, the term "biological function" refers to the structural, mechanical or metabolic activity of a tissue or organ. Extracorporeal devices of the present invention can comprise hybrid devices suitable for both ex vivo and in vivo use.

Tissue engineered structures of the invention can be implanted into a host. The structures optionally have connections for flow into and out of the vasculature, which, upon implantation, allow for the vasculature to be anastomized into the existing vasculature, thereby providing an immediate blood supply for the implanted organ equivalent. Accordingly, implantable structures can be transferred into animals or patients by directly or indirectly connecting the blood vessels to enable flow into and out of the vasculature.

Extracorporeal devices may provide a partial support function, which can extend the time between hospital treatments for patients on chronic organ support therapies and improve the quality of life between hospital treatments. For example, the designs can be adapted to produce an extracorporeal renal dialysis device, an extracorporeal liver device, or an extracorporeal artificial lung device. Such devices may or may not be supported with living cells loaded or seeded into the device.

ADDITIONAL REFERENCES

1. B. Chehroudi, D. McDonnell and D. M. Brunette, "The effects of micromachined surfaces on formation of bone-like tissue on subcutaneous implants as assessed by radiography and computer image processing," J. Biomed. Mater. Res. 34 279 (1997.)
2. C. Oakley, N. A. F. Jaeger and D. M. Brunette, "Sensitivity of Fibroblasts and Their Cytoskeletons to Substratum Topographies: Topographic Guidance and Topographic Compensation by Micromachined Grooves of Different Dimensions," Exper. Cell Res. 234 413 (1997.)
3. Y. Ito, "Surface micropatterning to regulate cell functions," Biomaterials 20 2333 (1999.)
4. X. Y. Jiang, S. Takayama, X. P. Qian, E. Ostuni, H. K. Wu, N. Bowden, P. LeDuc, D. E. Ingber and G. M. Whitesides, "Controlling mammalian cell spreading and cytoskeletal arrangement with conveniently fabricated continuous wavy features on poly(dimethylsiloxane)." Langmuir 18 3273 (2002.)
5. M. J. Dalby, M. O. Riehle, H. Johnstone, S. Affrossman and A. S. Curtis, "In vitro reaction of endothelial cells to polymer demixed nanotopography," Biomaterials 23 2945 (2002.)
6. S. Mosler, N. Gadegaard, N. B. Larsen, "Improving substratum-adherence of living cells by surface nanoengineering: Fibrillar collagen-coatings and topographical polymer-replicates," www.polymers.dk/research/posters/mosler.pdf

We claim:

1. A method of forming a device capable of organizing cells on a substrate for use in engineering tissue, said method comprising the steps of:
   a) generating micromachined surface structures on a substrate to increase the surface area of the substrate; and
   b) forming first and second nanotopographic features on portions of the micromachined surface structures in such a manner so as to permit organization of a first cell type on the first nanotopographic feature and a second cell type on the second nanotopographic feature to create subassemblies for use in constructing engineered tissue, wherein the first cell type is different from the second cell type.

2. The method according to claim 1, wherein the micromachined surface structures define the walls and floor of a channel.

3. The method according to claim 1, wherein the step of forming nanotopographic features includes arranging the nanotopographic features in predefined locations on the substrate.

4. The method according to claim 1, wherein the step of forming nanotopographic features includes orienting the nanotopographic features to facilitate adhesion of one or more cell types to a desired location on the substrate.

5. The method according to claim 4, wherein the step of forming nanotopographic features includes arranging the nanotopographic features in predefined locations on the substrate.

6. The method according to claim 1, wherein the micromachined surface structures are of a micron scale.

7. The method according to claim 1, wherein the nanotopographic features are of a sub-micron scale.

8. A method of forming a device capable of growing cells with increased cell density, said method comprising the steps of:
   a) generating first micromachined surface structures on a first substrate to form a parenchymal chamber having a floor;
   b) superimposing first nanotopographic features on the floor to increase surface area of the parenchymal chamber;
   c) generating second micromachined surface structures on a second substrate to form a vascular network defining a vascular channel;
   d) separating the parenchymal chamber from the vascular network with a porous membrane; and
   e) forming a fluid communication between the vascular network and the parenchymal chamber.

9. A method according to claim 8, further comprising the steps of:
   f) seeding parenchymal cells on the floor of the parenchymal chamber; and
   g) clearing desired metabolic products of the parenchymal cells into the vascular channel through the porous membrane.

10. The method according to claim 8, further comprising the steps of:
    superimposing second nanotopographic features on the vascular channels; and
    seeding cells on the second nanotopographic features.

11. The method according to claim 9, further comprising the step of:
    h) slow flow seeding endothelial cells on the vascular channels.

12. The method according to claim 9, wherein the desired metabolic products of the cells are selected from the group consisting of cytokines, growth factors, and paracrine/endocrine factors and wherein the parenchymal cells are selected from the group consisting of hepatocytes, renal cells and combinations thereof.

13. The method according to claim 8, wherein the second micromachined surface structure defines the walls and floor of the vascular channel.

14. The method according to claim 8, wherein the step of superimposing the first nanotopographic feature includes arranging the nanotopographic features in predefined locations on the substrate.

15. The method according to claim 8, wherein the step of superimposing the first nanotopographic feature includes orienting the nanotopographic features to preferentially adhere one or more cell types to a desired location on the substrate.

16. The method according to claim 8, wherein the first nanotopographic features include a plurality of individual units that form a nanopattern.

17. The method according to claim 16, wherein:
    the nanopattern includes nanotopographic features arranged in periodic pattern arrays;

the nanotopographic features are selected from the group consisting of grooves, grids, pores, bumps and combinations thereof;

at least a portion of the nanotopographic features have a height, width and length that are less than 1 micron each; and at least a portion of the nanotopographic features have a diameter that is less than 1 micron.

18. The method according to claim 8, further including the step of surface patterning areas of the first and second substrates with chemical species.

19. The method according to claim 18, wherein the micromachined surface structures are of a micron scale and the nanotopographic features are of a sub-micron scale.

20. A method of growing cells for use in engineering tissue, said method comprising the steps of:
 a) generating first micromachined surface structures in a first layer to increase surface area;
 b) superimposing first nanotopographic features on the micromachined surface structures;
 c) generating second micromachined surface structures in a second layer to increase surface area;
 d) superimposing second nanotopographic features on the micromachined surface structures, wherein the second nanotopographic features are different from the first nanotopographic features;
 e) separating the first layer from the second layer with a porous membrane;
 f) seeding cells on the first and second layers; and
 g) clearing desired metabolic products of the cells on the first layer into the second layer through the porous membrane.

\* \* \* \* \*